(12) United States Patent
Tilstam et al.

(10) Patent No.: US 7,547,776 B1
(45) Date of Patent: *Jun. 16, 2009

(54) PROCESS FOR THE PRODUCTION OF FLUDARABINE-PHOSPHATE LITHIUM, SODIUM, POTASSIUM, CALCIUM AND MAGNESIUM SALTS AND PURIFICATION PROCESS FOR THE PRODUCTION OF FLUDARABINE-PHOSPHATE AND FLUDARABINE-PHOSPHATE WITH A PURITY OF AT LEAST 99.5%

(75) Inventors: Ulf Tilstam, Berlin (DE); Thomas Schmitz, Berlin (DE); Klaus Nickisch, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/471,040

(22) Filed: Dec. 23, 1999

Related U.S. Application Data

(62) Division of application No. 09/208,587, filed on Dec. 10, 1998, now Pat. No. 6,046,322.

(60) Provisional application No. 60/069,778, filed on Dec. 16, 1997.

(30) Foreign Application Priority Data

Dec. 11, 1997 (DE) ............................ 197 56 289

(51) Int. Cl.
*C07H 19/04* (2006.01)
*C07H 19/20* (2006.01)

(52) U.S. Cl. ..................... 536/26.7; 536/27.1

(58) Field of Classification Search ............... 536/55.3, 536/27.12, 26.71, 26, 27, 26.7, 27.1; 424/180
See application file for complete search history.

(56) References Cited

U.S. PATENT DOCUMENTS

| | | | |
|---|---|---|---|
| 3,703,507 A | 11/1972 | Haskell et al. | |
| 4,188,378 A | 2/1980 | Montgomery | 514/46 |
| 4,210,745 A | 7/1980 | Montgomery | 536/55.3 |
| 4,357,324 A * | 11/1982 | Montgomery et al. | 514/45 |
| 5,110,919 A * | 5/1992 | Blumbergs et al. | 536/27.11 |
| 5,296,589 A | 3/1994 | Blumberg | 536/27.7 |
| 5,506,352 A * | 4/1996 | Butler et al. | 536/55.3 |
| 6,046,322 A | 4/2000 | Tilstam et al. | |
| 6,174,873 B1 | 1/2001 | Wrenn, Jr. | |

FOREIGN PATENT DOCUMENTS

| | | |
|---|---|---|
| DE | 19543052 | 5/1997 |
| EP | 1047704 | 11/2000 |
| GB | 2124901 A | 2/1984 |
| WO | WO 91/08215 | 6/1991 |
| WO | WO 94/12514 | 6/1994 |
| WO | WO 97/18211 | 5/1997 |

OTHER PUBLICATIONS

Notice of Opposition to European Patent No. 1 047 704, Application No. 98965703.6, Mayne Pharma Pty, Ltd., Date of Mention Jan. 29, 2003.
Declaration of Donald Corcoran, dated Oct. 27, 2003.
Letter from Alltech Association Australia Pty, Ltd., dated Oct. 22, 2003 with declaration attached from Dr. Phillip J. Anevski, dated Oct. 23, 2003.
Letter from Boult Wade Tennant dated Oct. 29, 2003.
The Nucleic Acids Chemistry and Biology, vol. 1, 1955, chapter 6, pp. 211-241.
Exhibit C, Fludarabine Phosphate >99.5% Pure After Dowex 1X4 Column, Jul. 24, 2003, with attached, Waldo E. Cohn, The Anion-Exchange Separation of Ribonucleotides, 72 J. Am. Chem. Soc., pp. 1471-1478 (1950).
Waldo E. Cohn, Methods of Isolation and Characterization of Mono and Polynucleotides by Ion Exchange Chromatography, 107 Methods in Enzymology, pp. 724-743 (1967).
In the House of Lords, *Biogen Inc.* v. *Medeva PLC*, dated Oct. 31, 1996, pp. 1-54.
Henry Herbert Cobb III, Stability of Fludarabine Phosphate, Pentostatin, and Amsacrine in Commonly Used Infusion Solutions and After Filtration, and Osmolality of Various Constituted Chemotherapeutic Agents pp. 20-48 (1995).
Boards of Appeal of The European Patent Office, Decision, Previously Presented. 20-48, Case No. T 0990/96-3.3.1. (Feb. 12, 1998).
The MERCK Index, Twelfth Edition, 1996, Fludarabine.
Official Monographs, USP 26, Fludarabine Phosphate, pp. 3096-3097 (1996).
Notice of Opposition to European Patent No. EP 1047704, App. No. 98965703.6, by Curtis, Phillip Anthony, Nov. 11, 2003.
Notice of Opposition to European Patent No. EP 1047704, App. No. 98965703.6, by Sicor, Inc., Date of Mention Jan. 29, 2003.

(Continued)

*Primary Examiner*—Elli Peselev
(74) *Attorney, Agent, or Firm*—Mullen, White, Zelano, Branigan, P.C.

(57) ABSTRACT

The present invention generally relates to a fludarabine-phosphate with a purity of at least 99.5%.

12 Claims, No Drawings

OTHER PUBLICATIONS

EP-B-1047704 Opposition by SICOR Inc., in European Patent No. 1047704, App. No. 98965703.6, Experimental Report, dated Oct. 29, 2003.
Information Statement 98965703.6; Jun. 15, 2005.
Letter to European Patent Office (from Boult Wade Tennant); Jun. 13, 2005.
Letter to European Patent Office (from J.A. Kemp & Co.); Apr. 14, 2005.
Letter to European Patent Office (from Boult Wade Tennant), Apr. 14, 2005.
Declaration of Dr. Andrew Malcolm Knill; Apr. 6, 2005.
Curriculum Vitae of Dr. Harald Rabe; Apr. 13, 2005.
Curriculum Vitae of Dr. Ulf Peter Tilstam; Apr. 13, 2005.
EPO appeal, oral proceedings (Jun. 2005) and results, pp. 1-73.
Patentee grounds for appeal of Nov. 30, 2005.
"Fludarabine Phosphate," European Pharmacopoeia 5.1; Apr. 2005:1781. (OD30).
Tabelle 1; Nov. 30, 2005. (OD31).
Tabelle 2; Nov. 30, 2005. (OD32).
Report on the Public Hearing of the Technical Board of Appeals Mar. 3, 2008 on Mar. 8, 2007.
Ruling of the Technical Board fo Appeals Mar. 3, 2008 of Mar. 8, 2007.
Weickmann & Weickmann letter to European Patent Office Feb. 8, 2007 regarding Appeal No. T1393/05-Mar. 3, 2008.
Statement by Dr. Michael Harre, In Re EP 1 047 704 B1 of Jan. 30, 2007.
Statement by Dr. Thomas Wessa, In Re EP 1 047 704 B1 of Feb. 2, 2007.
Statement by Professor Siegfried Blechert, In Re EP 1 047 704 B1 of Feb. 2, 2007.
Statement by Professor Reinhard Schomacker, In Re EP 1 047 704 B1 of Feb. 1, 2007.
Statement by Professor Ulf Tilstam, In Re EP 1 047 704 B1 of Feb. 1, 2007.
Tentative opinion of Technical Board of Appeals (2007).
Appeal Observation (Opponent 01) in EP-B- 1047704, Opposition—Apr. 24, 2006.
Observation by Opponent III in Appeal in EP-B- 1047704, Opposition—Jun. 19, 2006.
Additional Krill Declaration (OD33) in EP-B- 1047704, Opposition—Apr. 24, 2006.
Bigatti Declaration (Ex. A and B) (OD35) in EP-B- 1047704, Opposition—Jun. 12, 2006.
James M. Foran, David Oscier, Jennifer Orchard, Pharmacokinetic study of single doses of oral fludarabine phosphate in patients with "low-grade" non-hodgkin's lymphoma, *Journal of Clinical Oncology*, May 1999, pp. 1574-1579.

* cited by examiner

PROCESS FOR THE PRODUCTION OF FLUDARABINE-PHOSPHATE LITHIUM, SODIUM, POTASSIUM, CALCIUM AND MAGNESIUM SALTS AND PURIFICATION PROCESS FOR THE PRODUCTION OF FLUDARABINE-PHOSPHATE AND FLUDARABINE-PHOSPHATE WITH A PURITY OF AT LEAST 99.5%

This is a division of application Ser. No. 09/208,587, filed Dec. 10, 1998, now U.S. Pat. No. 6,046,322. This application claims the benefit of the filing date of U.S. provisional application Ser. No. 60/069,778, filed Dec. 16, 1997.

The invention relates to a process for the production of fludarabine-phosphate lithium, sodium, potassium, calcium and magnesium salts that can be used as intermediate products for the purification of FLUDARABINE-PHOSPHATE, and fludarabine-phosphate with a purity of at least 99.5%.

Fludarabine-phosphate is the "International Nonproprietary Name" (INN) of 9-β-D-arabinofuranosyl-2-fluoroadenine-5'-O-dihydrogenphosphate. The first synthesis of the precursor of fludarabine-phosphate, 9-β-D-arabinofuranosyl-2-fluoroadenine, is described in U.S. Pat. No. 4,188,378. This substance has strongly cytotoxic properties, and various derivatives of it were produced with the purpose of reducing side-effects. The 5'-phosphate (prodrug), thus the fludarabine-phosphate and its production, is described within U.S. Pat. No. 4,357,324. In further publications, for example U.S. Pat. No. 4,210,745, WO 91/08215 and WO 94/12514, alternative production processes are disclosed.

The production method that is used at this time starts from 9-β-D-arabinofuranosyl-2-fluoroadenine that is reacted with trimethylphosphate and phosphoroxychloride (phosphorylation). These educts are brought to reaction and then crystallized from water. The temperature of approximately 75° C. that is to be used in the recrystallization destroys a portion of the substance, since fludarabine-phosphate is thermally unstable in water at this temperature. It is further disadvantageous that this recrystallization that is known from the prior art results only in weak improvement of purity, and even for technical production, the process can be implemented only in batch sizes of approximately below 1 kg. The salts of fludarabine-phosphate that are described within DE 41 41 454 A1 cannot be produced according to the teaching of this publication. If the described reaction conditions were used, mainly cleavage of phosphoric acid in the molecule would result.

In U.S. Pat. No. 5,296,589, the water solubility of the sodium salt of fludarabine-phosphate (2-fluoro-ara-adenosine 5'-phosphate) is described in column 10, lines 37-40. It is further described in column 9, lines 61-69 that the salt cannot be purified by recrystallization from water, since these conditions would result in destroying the compound (see also DE 195 43 052 A1, WO 92/0312 A1 and U.S. Pat. No. 5,506,352).

The object of this invention is to provide a purification process that results in considerably improved quality (purity) of fludarabine-phosphate and that in an industrial-scale process can easily be applied even to quantities of more than one kilogram.

This object is achieved according to the teaching of the claims.

The invention relates to a process for the production of fludarabine-phosphate lithium, sodium, potassium, calcium and magnesium salts, whereby fludarabine-phosphate is suspended in water, an alkali or alkaline-earth basic solution is added to this solution while being stirred and at temperature of below 30° C., and this solution is slowly poured into acetone that is 45-55° C., cooled, and the deposited precipitate is optionally filtered and optionally dried, and further to a process for the production of fludarabine-phosphate, whereby the lithium, sodium, potassium, calcium and magnesium salts are produced according to a process for the production of fludarabine-phosphate lithium, sodium, potassium, calcium and magnesium salts, whereby fludarabine-phosphate is dissolved in water, an alkali or alkaline-earth basic solution is added to this solution while being stirred and at temperatures of below 30° C., and this solution is slowly poured into acetone that is 45-55° C., cooled, and the deposited precipitate is optionally filtered and optionally dried and then are released with mineral acid.

Used as suitable bases are hydroxides and carbonates of alkalis or alkaline-earths, which are readily soluble in water; for example, lithium, sodium, potassium or calcium hydroxide; sodium or potassium carbonate.

As has been found, surprisingly enough, alkali and alkaline-earth salts of fludarabine-phosphate can be produced as stable, crystalline and readily characterizable substances that can be purified by crystallization. It has been shown that these alkali and alkaline-earth salts of fludarabine-phosphate can be isolated with ease; the latter withstand even prolonged storage without showing instability. Especially suitable are lithium, sodium, potassium, calcium and magnesium salts.

Here, it has proven to be advantageous that this crystallization takes place especially readily from water/acetone. Thus, fludarabine-phosphate is dissolved by adding sodium carbonate solution or the analogous basic solutions of the other elements and is poured into this aqueous solution in acetone. For example, 6.1 kg of fludarabine-phosphate is suspended in 35 l of water; 1.79 kg of sodium carbonate, dissolved in 7.9 l of water, is added, and this solution is poured into 150 l of acetone at 45-55° C., preferably at 50° C. The temperature must never exceed 60° C., since otherwise the substitution of fluorine by hydroxyl is carried out as a secondary reaction, which is undesirable. When the mixture is cooled, the NON-phosphated derivatives remain in solution, and the desired product crystallizes.

When dissolved in water, these fludarabine-phosphate salts of the alkalis and alkaline-earths produce solutions that are not strongly acidic but rather almost neutral. The recycling of these salts in free fludarabine-phosphate can easily be carried out by mixing with strong mineral acid. As mineral acids, for example, hydrochloric acid, sulfuric acid, nitric acid or phosphoric acid are used. When the free bases are released, the MULTIPLY phosphated by-products remain in solution.

The claimed salts of fludarabine-phosphate can easily be stored as precursors of fludarabine-phosphate for a prolonged time, and the active ingredients are released if necessary.

The invention also relates to fludarabine-phosphate with a purity of at least 99.5%. According to the prior art, the active ingredient previously could be obtained only at a purity of about 98.0-98.5%. It is impossible, by the conventional crystallization process, for example from water, to exceed a degree of purity of 98.5%, even though the same batch is crystallized several times. This conventional purification method is problematical in nature if the period for heating and filtration of the, for example, aqueous solution requires too much time; these are periods of 25 minutes and more. In this case, it results in the formation of various contaminants, rubberlike materials, which can no longer be removed by crystallization methods.

Fludarabine-phosphate purities of, for example, 99.5; 99.55; 99.6; 99.65; 99.7; 99.75; 99.8; 99.9 or 99.95% can be obtained by the process according to the invention, even if fludarabine-phosphate is purified only one time according to the process of the invention. It is also possible, however, to use the process for a fludarabine-phosphate batch two and more times.

The following examples are intended to explain the invention in more detail:

EXAMPLE 1

Fludarabine-Phosphate-Disodium Salt 5.0 g of fludarabine-phosphate at a purity of 98.5% is suspended in 30 ml of water and stirred for about 3-5 minutes. 6.5 ml of a soda solution (18.5% by weight) is added to this suspension while being stirred and at temperatures of below 30° C. After the addition has been completed, the mixture is stirred for 15 minutes and then undissolved material is filtered out. The clear solution that is thus obtained is slowly poured into acetone (at 50° C.). It is stirred for 2 more hours and cooled. The deposited precipitate is filtered, washed with acetone and dried; 5.0 g of fludarabine-phosphate disodium salt, 98% of theory, is obtained.

Melting point 235° C.; purity: 98.5%
Analysis: Cld: for $C_{10}H_{11}FNa_2N_5O_7P \times 2H_2O$ (445.20)
C, 26.98; H, 3.39; F, 4.27; N, 15.73; P, 6.96; Na 10.33
Fnd: C, 27.15; H, 3.93; N, 15.72; Na 9.65; P 6.15
IR (KBr): 3420, 3340, 3200, 2910, 1650, 1610, 1390, 1210, 1100 and 980 cm$^{-1}$.
NMR (D$_2$O): 4.05-4.22 m (3H; H-4'; both H-5'); 4.45-4.60 m (2H; H-2' and H-3'); 6.2 d (1H; H-1'); 8.45 s (1H; H-8).

EXAMPLE 2

Release of Fludarabine-Phosphate from the Disodium Salt 5.0 g of fludarabine-phosphate disodium salt according to Example 1 is dissolved in 35 ml of water within 3-5 minutes. The solution is filtered, mixed slowly with 5 ml of hydrochloric acid (37%) and stirred for 1-2 hours. The deposited precipitate is suctioned off and washed with ice water and ethanol, and 4.0 g of fludarabine-phosphate, 90% of theory, is produced.

Melting point 202-203° C.; purity: 99.6%.
Analysis, Cld: $C_{10}H_{13}FN_5O_7P$ (365.21)
C, 32.89; H, 3.59; N, 19.17; F, 5.20: P 8.48
Fnd: C, 32.81; H, 3.65; N, 19.03; P, 8.41
IR (KBr): 3443, 3326, 3123, 2925, 2950-2100, 1663, 1591, 1211, 1126 and 1050 cm$^{-1}$.
NMR (DMSO): 3.94-3.99 m (1H; H-4'); 4.06-4.14 m (3H; H-3'; both H-5'); 4.14-4.18 m (1H; H-2'); 5.4-6.1 broad (OH protons); 6.17 d (1H; H-1'); 7.6-8.0 broad (NH protons); 8.14 s (1H; H-1') 9-11 broad (P—OH).

EXAMPLE 3

Fludarabine-Phosphate Dilithium Salt 10.0 g of fludarabine-phosphate at a purity of 97.4% is suspended in 70 ml of water within about 5 minutes and mixed with an aqueous lithium-hydroxide solution (10%). This solution is stirred for one hour at room temperature and then filtered. The clear solution that is thus obtained is poured into 250 ml of acetone (at 50° C.) and stirred for 1 more hour. The deposited precipitate is filtered, washed with acetone and after drying, 4.3 g of fludarabine-phosphate-dilithium salt is produced. (90% of theory).

Melting point 0.240-260° C.; purity: 98.5%.

Analysis: Cld: for $C_{10}H_{11}FLi_2N_5O_7P \times 3H_2O$ (431.12)
C, 27.86; H, 3.98; F, 4.41; N, 16.25; P, 7.18; Li, 3.22
Fnd: C, 27.15; H, 3.86; N, 15.76; Li, 3.05; P 6.72
NMR (D$_2$O): 4.05-4.22 m (H-4'; H-5'); 4.45-4.55 m (H-2' and H-3'); 6.25 d (H-1'); 8.50 s (H-8)
The release according to Example 2 results in a fludarabine-phosphate purity of 99.85%.

EXAMPLE 4

Fludarabine-Phosphate-Dipotassium Salt 5.0 g of fludarabine-phosphate at a purity of 96.1% is dissolved in 30 ml of water, and 6.5 ml of a potassium carbonate solution (18.5% by weight) is added to this solution below 30° C. It is stirred for 15 more minutes, then solid material is filtered out. The clear solution that is thus obtained is poured into acetone at 50° C., cooled to room temperature and stirred for 2 more hours. The deposited precipitate is filtered and washed twice with acetone. 4.5 g of fludarabine-phosphate dipotassium salt is obtained.

Melting point 220-230° C.; purity: 98.55%.
IR (KBr): 3420, 3340, 3200, 2910, 1650, 1610, 1390, 1210, 1100 and 980 cm$^1$.
NMR (D$_2$O): 4.0-4.2 m (H-4'; H-5'); 4.4-4.60 m (H-2' and H-3'); 6.25 d (H-1'); 8.5 s (H-8).
The release according to Example 2 results in a fludarabine-phosphate purity of 99.80%.

EXAMPLE 5

Fludarabine-Magnesium Salt 10.0 g of fludarabine phosphate at a purity of 97.5% is suspended in 100 ml of water within about 5 minutes, and magnesium oxide is added to this solution. The mixture is stirred for one more hour at room temperature and then filtered. The clear solution is poured into 200 ml of acetone, stirred for 1 more hour, and the crystallizate is separated by filtration. 10.0 g (95% of theory) of the fludarabine-phosphate magnesium salt is obtained.

Melting point: 260° C.; purity: 98.45%.
Analysis: Cld., for $C_{10}H_{11}FMgN_5O_7P \times 2H_2O$ (423, 525)
C, 28.36; H, 3.57; F, 4.49; Mg, 5.74; N, 16.54; P, 7.31
Fnd: C, 27.99; H, 3.92; Mg, 5.54; N, 16.38;
IR (KBr): 3420, 3340, 3200, 2910, 1650, 1610, 1390, 1210, and 980 cm$^{-1}$.
NMR (D$_2$O): 4.0-4.2 m (H-4'; H-5'); 4.5-4.60 m (H-2' and H-3'); 6.2 d (H-1'); 8.4 s (H-8).
The release according to Example 2 results in a fludarabine-phosphate purity of 99.55%.

The invention claimed is:
1. Crystalline fludarabine-phosphate with a purity of at least 99.5%.
2. Crystalline fludarabine-phosphate with a purity of greater than 99.55%.
3. Crystalline fludarabine-phosphate with a purity of greater than 99.6%.
4. Crystalline fludarabine-phosphate with a purity of greater than 99.7%.
5. Crystalline fludarabine-phosphate with a purity of greater than 99.8%.
6. Crystalline fludarabine-phosphate with a purity of greater than 99.85%.
7. Crystalline fludarabine-phosphate of claim 2 obtained in a quantity greater than one kilogram.

8. Crystalline fludarabine-phosphate of claim 3 obtained in a quantity greater than one kilogram.

9. Crystalline fludarabine-phosphate of claim 4 obtained in a quantity greater than one kilogram.

10. Crystalline fludarabine-phosphate of claim 5 obtained in a quantity greater than one kilogram.

11. Crystalline fludarabine-phosphate of claim 6 obtained in a quantity greater than one kilogram.

12. Crystalline fludarabine-phosphate of claim 1 obtained in a quantity greater than one kilogram.

* * * * *